United States Patent
Bärnreuther et al.

(10) Patent No.: US 9,742,840 B2
(45) Date of Patent: Aug. 22, 2017

(54) INTEGRATION OF USER INTERFACES FOR DIFFERENT PHYSICALLY DISTRIBUTED MEDICAL APPLICATIONS

(71) Applicant: Siemens Aktiengesellschaft, Munich (DE)

(72) Inventors: Rainer Bärnreuther, Nuremburg (DE); Ivan Murphy, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 304 days.

(21) Appl. No.: 14/494,740

(22) Filed: Sep. 24, 2014

(65) Prior Publication Data

US 2015/0180951 A1 Jun. 25, 2015

(30) Foreign Application Priority Data

Dec. 20, 2013 (EP) .................................... 13198719

(51) Int. Cl.

| | |
|---|---|
| *H04L 29/08* | (2006.01) |
| *G06F 9/44* | (2006.01) |
| *G06F 21/53* | (2013.01) |
| *H04L 29/06* | (2006.01) |
| *G06F 19/00* | (2011.01) |
| *G06F 3/048* | (2013.01) |
| *G06F 9/445* | (2006.01) |

(52) U.S. Cl.
CPC .............. *H04L 67/10* (2013.01); *G06F 3/048* (2013.01); *G06F 9/44* (2013.01); *G06F 9/4443* (2013.01); *G06F 9/4451* (2013.01); *G06F 19/3406* (2013.01); *G06F 21/53* (2013.01); *H04L 63/0815* (2013.01); *G06F 2221/2145* (2013.01)

(58) Field of Classification Search
CPC ... H04L 67/10; H04L 63/0815; G06F 9/4451; G06F 9/4443; G06F 21/53; G06F 9/44; G06F 19/3406; G06F 3/048; G06F 2221/2145
See application file for complete search history.

(56) References Cited

U.S. PATENT DOCUMENTS

| | | | | |
|---|---|---|---|---|
| 6,381,579 | B1 * | 4/2002 | Gervais ............ | G06Q 10/06311 705/7.13 |
| 7,721,303 | B2 * | 5/2010 | Alves de Moura ....... | G06F 8/38 709/202 |
| 8,214,747 | B1 * | 7/2012 | Yankovich ............ | G06F 9/4451 715/751 |
| 9,210,040 | B2 * | 12/2015 | Mikkilineni ........ | H04L 41/0886 |
| 2003/0074580 | A1 * | 4/2003 | Knouse ............... | H04L 63/0815 726/4 |

(Continued)

*Primary Examiner* — Brian J Gillis
*Assistant Examiner* — Javier O Guzman
(74) *Attorney, Agent, or Firm* — Harness, Dickey & Pierce P.L.C.

(57) ABSTRACT

A system, method and computer program product are disclosed for integrating a user interface of external or foreign applications, running on second physical machines, into a user interface of a first application running on a first physical machine. In an embodiment, the generated integrated user interface is displayed on a monitor of the first physical machine. The applications refer to MR-scanning and post-processing applications. The user is only working with one single, common and integrated user interface although he controls two different sets of applications on different machines.

19 Claims, 10 Drawing Sheets

(56) References Cited

U.S. PATENT DOCUMENTS

| | | | |
|---|---|---|---|
| 2003/0229522 A1* | 12/2003 | Thompson | G06Q 10/067 705/4 |
| 2009/0007250 A1* | 1/2009 | Pouzin | G06F 21/335 726/10 |
| 2011/0029623 A1* | 2/2011 | Ax | G06F 9/4843 709/206 |
| 2011/0238618 A1* | 9/2011 | Valdiserri | G06F 19/321 707/608 |
| 2011/0271062 A1* | 11/2011 | Chen | G06F 3/061 711/154 |
| 2013/0212665 A1* | 8/2013 | Goyal | G06F 21/41 726/8 |
| 2014/0019891 A1* | 1/2014 | Borah | G06F 8/30 715/762 |

* cited by examiner

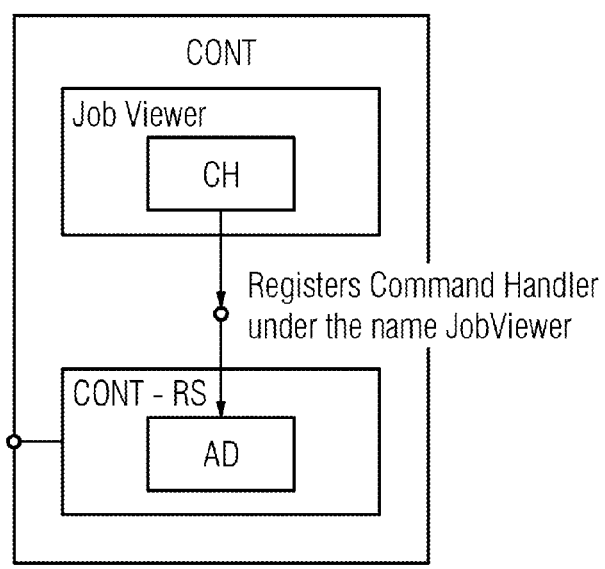
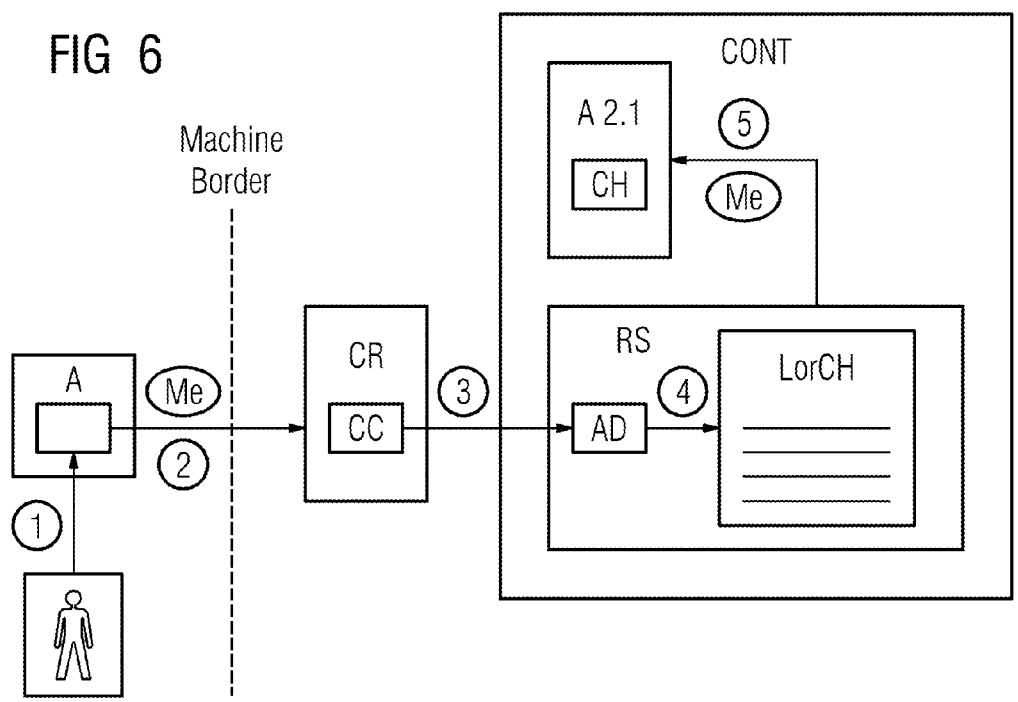

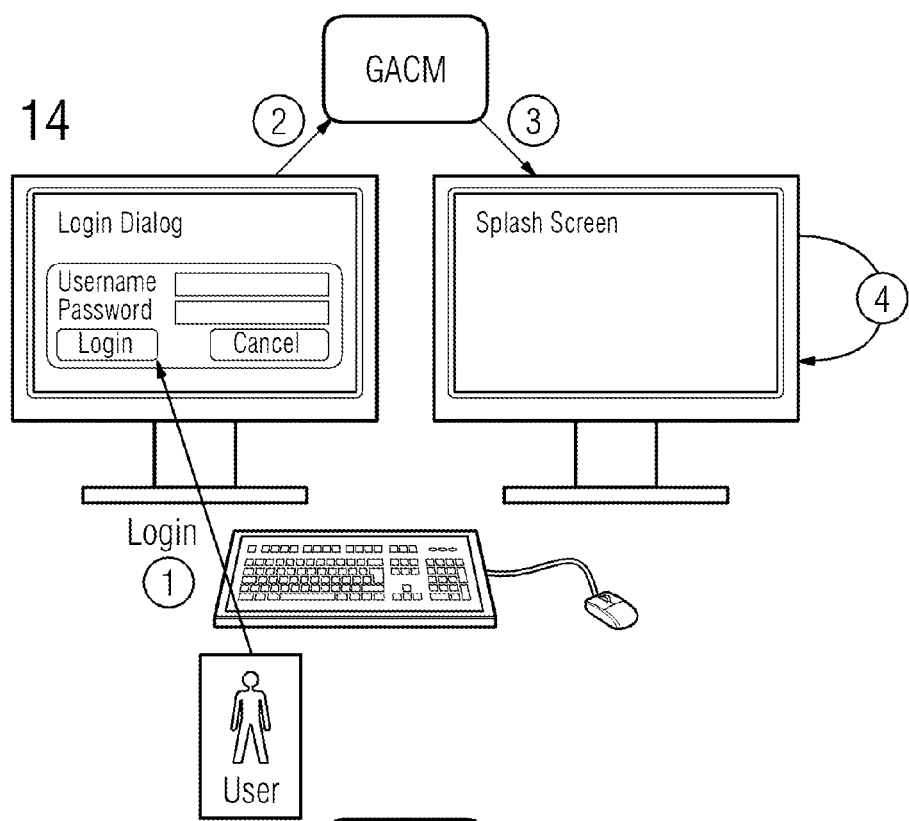
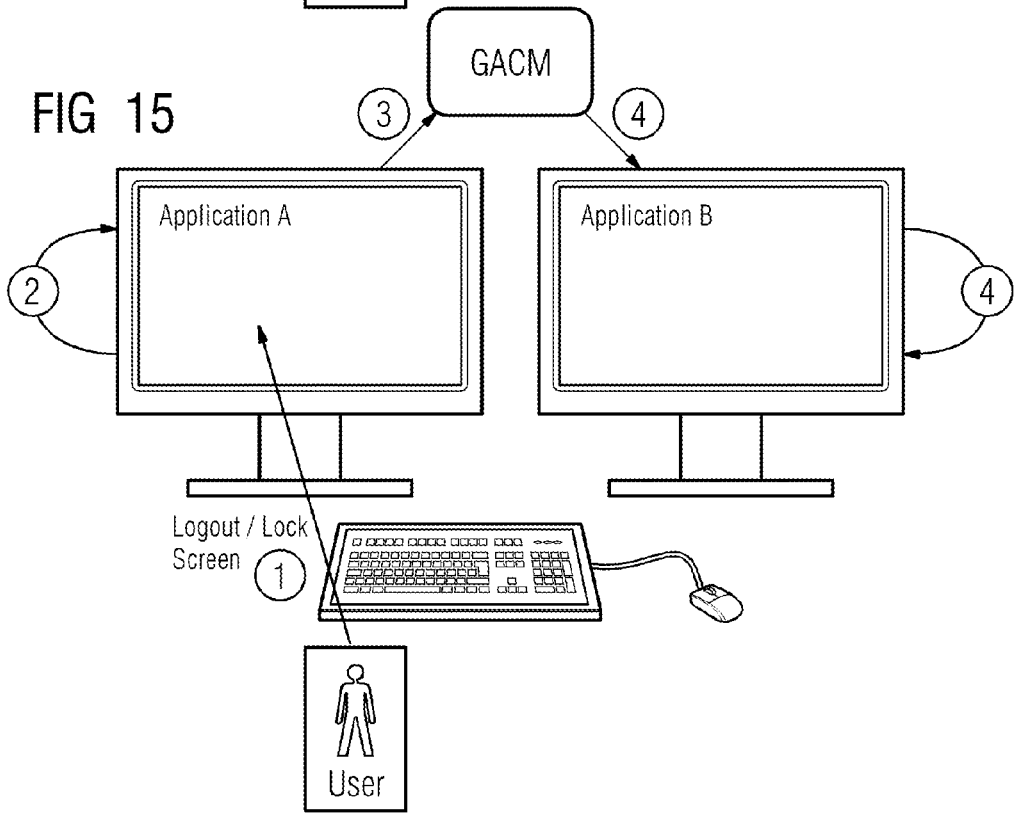

INTEGRATION OF USER INTERFACES FOR DIFFERENT PHYSICALLY DISTRIBUTED MEDICAL APPLICATIONS

PRIORITY STATEMENT

The present application hereby claims priority under 35 U.S.C. §119 to European patent application number EP 13198719.0 filed Dec. 20, 2013, the entire contents of which are hereby incorporated herein by reference.

FIELD

At least one embodiment of the present invention refers to the fields of medical technology and information technology and in particular to a method, system and/or a computer program product for integrating different user interfaces for different medical applications which are distributed across multiple physical machines. In particular, the invention relates to the session layer of the ISO/OSI-layer model by providing an improved process communication with synchronized data exchange between different physical systems.

The applications refer to scanner applications, like applications for magnetic resonance scanners, computer tomography devices, x-ray scanners, ultrasound imagers and other acquisition devices.

BACKGROUND

With respect to the image acquisition modalities, like MR scanners and the like manly two major categories of operations and activities have to be carried out: First, the control of the imaging device (e.g. MR scanner) as such and second, the processing of the acquired images (typically referred to as post-processing). Both, the control of the scanner as well as the post-processing are executed by means of a computer. This is why the MR scanner is delivered with a controlling workstation and a processing workstation.

Up to now, there has been a strict separation between the control of the scanner on the one hand and the post-processing of the acquired data on the other hand. For this reason at least two different workstations were provided.

In the new MR scanner generation, however, no longer two separated systems should be provided but one single computer based system, in particular one single workstation for both the scanner control and the post-processing tasks. However, the applications are still running on different systems.

SUMMARY

Therefore, the inventors have recognized that it is necessary to change the user interfaces for controlling the two different categories of applications (scanner control and post processing).

In particular, at least one embodiment of the present application tackles the issue on how the user interfaces of two different applications, which are running on two distinct systems could be presented to the user as one integrated user interface, although the applications are running on two physically separated machines and are visible on two collocated monitors. Although the setup includes two machines they shall be controlled with the same input devices (i.e. only one mouse and one keyboard is attached to the systems) and with one common user interface At least one embodiment of the present invention refers to a system for integrating different user interfaces for different medical applications which are distributed across multiple physical machines, wherein a first set of applications is assigned to (or running on) a first machine and a second set of applications is assigned to a second machine. All the applications (including the one running on the first machine and the ones running on the second machine) are controlled by a common single user interface, so that the user has the impression to work with one single workstation, although there are two or more workstations.

In at least one embodiment, the system comprises:
 a container configured to provide a common runtime infrastructure for hosting applications, comprising the first and second set of applications, wherein the container comprises:
  a remoting service (also called a container remoting service), configured to enable applications running inside the container to register a command handler for executing the respective application logic of the application;
 a command receiver, configured to offer an interface for receiving commands which have been input by a user interface of one of the first set of applications and provide an interface to one of the second set applications in the container as the command is to be executed by at least one application of the second set of applications; and
 a hierarchical cross machine context management system for sharing context data, comprising:
  a global context manager, responsible for sharing context data across different physical machines,
  a machine local context manager, responsible for sharing context data across different applications residing on the same physical machine, and
  an application local context manager, responsible for sharing context data across different components which are running within the same application.

Another example embodiment of the present invention refers to a computer-implemented method for integrating a user interface for a set of second applications in a user interface for a set of first applications, wherein the applications are different medical applications which are distributed across multiple physical machines, wherein the first set of applications is assigned to a first machine and the second set of applications is assigned to a second machine, comprising the steps of:
 Receiving a user command on the user interface of a first application
 Based on the received user command, generating a command message
 Forwarding the generated command message via a command receiver to a container, in which the second set of applications are hosted
 Executing the command on a receiving application in the container
 Providing an integrated user interface for the first and second set of applications on the first machine.

Another example embodiment of the present invention refers to a non-transitory computer-readable medium having stored thereupon a computer program for integrating a user interface for a set of second applications in a user interface for a set of first applications, wherein the applications are different medical applications which are distributed across multiple physical machines, wherein the first set of applications is assigned to a first machine and the second set of applications is assigned to a second machine, the computer program comprising computer program code which, when run on one of the machines causes the machine to:
  receive a user command on the user interface of a first application
  based on the received user command, to generate a command message
  forward the generated command message via a command receiver to a container, in which the second set of applications are hosted
  execute the command on a receiving application in the container
  provide an integrated user interface for the first and second set of applications on the first machine.

Another example embodiment of the present invention refers to a computer program for executing the method for providing an integrated user interface of different applications, as mentioned above. Thus, another aspect of the invention is to be seen in a computer program being loadable in a memory of a computer, wherein the computer program is adapted to carry out the steps of the method as mentioned above.

The computer program may be stored on a computer readable memory or storage device.

BRIEF DESCRIPTION OF THE DRAWINGS

The figures illustrate principles of the invention according to specific embodiments. Thus, it is also possible to implement the invention in other embodiments, so that these figures are only to be construed as examples. Moreover, in the figures, like reference numerals designate corresponding modules or items throughout the different drawings.

FIG. 5 is a schematic drawing of modules within a container, FIG. 6 is a schematic view for an example embodiment for a Job viewer application by doing a run-through with the Job Viewer example for a user wants to see the DICOM send jobs for a dedicated patient, FIG. 14 represents a master-slave deployment for visualizing a splash screen and FIG. 15 represents a process flow for an exemplary logout command.

DETAILED DESCRIPTION OF THE EXAMPLE EMBODIMENTS

Figure 1:
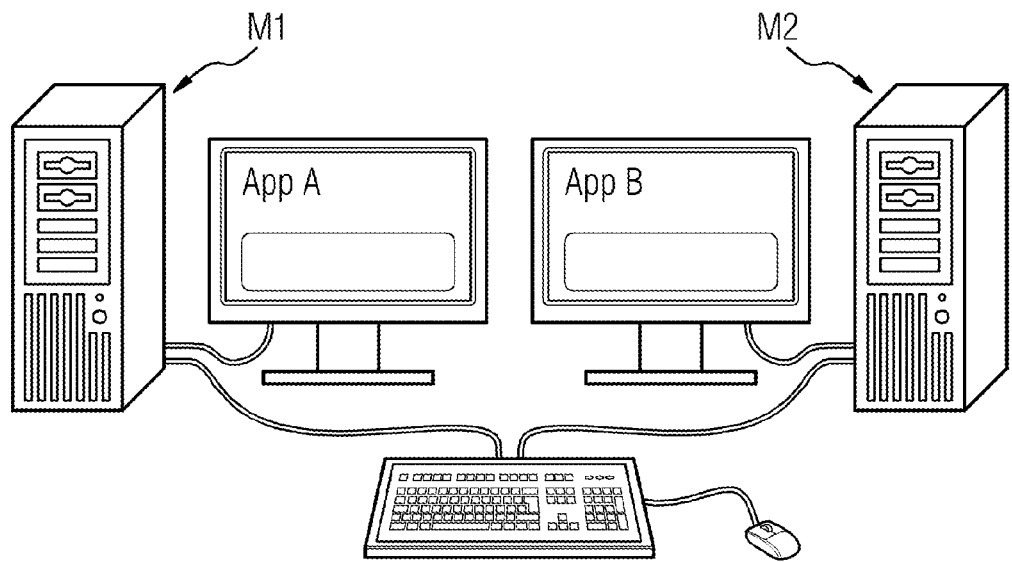
FIG. 1 is a schematic diagram according to one embodiment of a computer implemented system used for two different machines hosting different medical applications.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In at least one embodiment, the system comprises:
a container configured to provide a common runtime infrastructure for hosting applications, comprising the first and second set of applications, wherein the container comprises:
a remoting service (also called a container remoting service), configured to enable applications running inside the container to register a command handler for executing the respective application logic of the application;
a command receiver, configured to offer an interface for receiving commands which have been input by a user interface of one of the first set of applications and provide an interface to one of the second set applications in the container as the command is to be executed by at least one application of the second set of applications; and a hierarchical cross machine context management system for sharing context data, comprising:
   a global context manager, responsible for sharing context data across different physical machines,
   a machine local context manager, responsible for sharing context data across different applications residing on the same physical machine, and
   an application local context manager, responsible for sharing context data across different components which are running within the same application.

The system provides an integrated user interface for the first and second set of applications on the first machine.

At least one embodiment of the present invention relates to a system, method and/or computer program product for integrating a user interface of at least one external or foreign application ("external" refers to an application which is running, executed or hosted on an external machine, also called second or right application), running on at least one second physical machine into a user interface of a first (or left) application running on a first physical machine. The generated integrated user interface is displayed on at least one monitor of the first physical machine. The applications refer to MR- or CT-scanning applications and post-processing applications. The technical effect is, that although the user is only working with one single, common and integrated user interface, he controls two different sets of applications (first and second applications), which are hosted on different machines. Particularly, two different machines are used, one for controlling the imaging apparatus, like the MR/CT-scanner, and one for post-processing or pre-processing tasks, like e.g. advanced visualization applications.

User input, which is received on the generated common user interface, which is shown on the first (left) machine, is directed to the first application(s) and re-directed to the second application(s). In a preparation phase it may be configured, which of the two sets of application should share their context and to which extent and for which applications an automatic re-direction of user input should be executed (e.g. for an Online Help, Login/Logout/Screenlock and/or a Job Viewer application as a foreign post-processing application).

A session manger guarantees that in case of a system crash or shutdown the context data are re-usable again by means of at least three instances of application context managers.

This two machine setup is a typical deployment for scanners (e.g. for native.syngo based scanners). The user interface of the scanner application is running on the first (also called left) monitor and the user interface for (e.g. syngo.via) post-processing applications are running on the second (also called right) monitor. Although from an architecture point of view both applications are more or less independent and only loosely coupled through dedicated remote interfaces, the user shall have the impression to work with one integrated application spanning over two monitors.

In the following a short explanation of terms is given.

The first application(s) or the first set of applications refer to scanner applications. The first applications are directly controlling the scanner. Examples of these first applications are: Automatic selection of a scan protocol with the sequence of technical scanner configurations, execution of scans, triggering and controlling a Recon-Job for generation of raw DICOM image data (DICOM: Digital Imaging and Communications in Medicine) or control of the injection of contrast agents during a scan etc.

The second application(s) or the second set of applications refer/s to post or preprocessing applications. The second applications are processing data, which have been acquired by the scanner. Examples of these second applications comprise: a "job viewer" application and a "show patient details" application.

The integrated user interface which is provided and generated for the two different set of applications, running on different machines may be a graphical user interface. The integrated user interface is provided on the first machine. However, in an alternative setting it may also be possible to provide the user interface on the second machine (which comprises an indirect control of the first machine as well).

The container is a kind of intermediary node or agent and is the host of a plurality of different applications. It provides services and infrastructure, e.g. Logging, security, configuration management etc. It is constructed generically and enables the applications to be hosted inside, wherein the hosted applications may exchange data as well. According to a example embodiment the container and a command receiver are running on the same machine, in particular on the second machine.

The remoting service is a service which may be used by different entities. The remoting service enables to call or request dedicated functions or services of the container from an external process outside the container (but on the same machine). Further, the remoting service enables the remote control of selected applications inside the container. Each application may be configured in order to define which of its functionality it wants to provide to outside via the command handlers.

The remoting service provides two interfaces:
1. an internal interface through which applications/components running inside the container can register command handlers;
2. an external interface which allows applications running on the same machine to send commands to applications running inside the container.

The Command Receiver is a second process running on the same machine as the Container, preferably on the second (post-processing related) machine. The Command Receiver component offers an interface which can be accesses by external applications through different protocols like http, local command line or WCF (Windows Communication Foundation), with further supported protocols like SOAP, TCP/IP etc. External applications send messages that are targeted to for application/components running inside the Container to the Command Receiver. The Command Receiver is responsible to forward these messages to the Container.

The Command Handler is adapted for providing and executing the respective application or business logic. For example the Command Handler of a "Job Viewer" application would ensure that:
   a) the Job Viewer application is switched in the foreground of a user interface or on the first level and
   b) there is executed a filtering for the selected patient.

The Command Handler parses the message(s) he receives and executes the requested functionality.

The context management system is adapted a cross machine application context integration to allow clustering of distributed applications.

An application context is a set of context data for a specific application. Usually, it comprises user context data and patient context data. Optionally, also other meta data may be included in the context data set. Generally, data is to be shared between distributed clustered applications. An Application Context contains very general information like the Identification of the logged in user as well as application specific information like the identities of patients which require a specific handling within the application cluster (e.g. the scan patient). An Application Context is only accessible for an application within the cluster—application outside of the cluster do not have access to it.

According to an example embodiment a respective lifecycle of the context data of the context manager is configured individually for each set of context data and non-volatile context data are provided persistently.

The following Application Context Manager Roles do exist:

Local Application Context Manager (LACM)
LACM is responsible for sharing Application Context information between different components which are running within the same application process.

Machine Local Application Context Manager (MLACM)
MLACM is responsible for sharing Application Context information between different processes running on the same physical machine.

Global Application Context Manager (GACM)
GACM is responsible for sharing Application Context information across one or more physical machines.

The following Context Types exist:

Local Application Context (LAC)
LAC is only shared between components within one process.

Machine Local Application Context (MLAC).
MALC is shared between processes running on one physical machine.

Global Application Context (GAC)
GAC is shared between applications running multiple physical machines which are connected via network.

According to another example embodiment, the integrated user interface is shown on one common or on different monitors, related to the first machine. The second alternative relates to the setting in which more than one monitor is used for the first machine (and thus a multi monitor system of the first machine, so that the user interface is distributed over a plurality of monitors).

According to another example embodiment, the command receiver receives commands on the generated integrated user interface and generates command messages in response to the received commands and forwards these command messages to the container applications for execution.

According to another example embodiment, the container is started on demand by a user or automatically by an operating system or on demand by the command receiver.

According to another example embodiment, the system is used for a single sign-on such as a user may sign-on to the second set of applications automatically via his sign-on to the first set of applications. Thus, the integrated user interface enables a user to sign-in or log-in to the left system (first machine) and this log-in command automatically is transferred to the second machine, which in response to receiving the long-in command of the first machine will also sing-in the user on the right (second) machine. It is no longer necessary, that the user has to input his log-in commands (e.g. ID, password etc.) for the second machine. The same holds for signing off the system.

According to another example embodiment, the system is used for a single sign-off such as a user may sign-off from the second set of applications automatically via his sign-off from the first set of applications.

Another option is to use the system for a single locking of the screens. According to another example embodiment, the system is used for a single screen lock such as a user may lock his screen in the second set of applications automatically via a screen lock command entered for the first set of applications.

According to another example embodiment, the system comprises a re-authentication mechanism in case of a system crash, so that for application restart due to a system crash the context data are retrieved automatically from the global context manager and without the necessity to re-authenticate the user again. This holds for the patient context data and as well for the user context data.

Another example embodiment of the present invention refers to a computer-implemented method for integrating a user interface for a set of second applications in a user interface for a set of first applications, wherein the applications are different medical applications which are distributed across multiple physical machines, wherein the first set of applications is assigned to a first machine and the second set of applications is assigned to a second machine, comprising the steps of:

Receiving a user command on the user interface of a first application

Based on the received user command, generating a command message

Forwarding the generated command message via a command receiver to a container, in which the second set of applications are hosted Executing the command on a receiving application in the container Providing an integrated user interface for the first and second set of applications on the first machine.

Another example embodiment of the present invention refers to a non-transitory computer-readable medium having stored thereupon a computer program for integrating a user interface for a set of second applications in a user interface for a set of first applications, wherein the applications are different medical applications which are distributed across multiple physical machines, wherein the first set of applications is assigned to a first machine and the second set of applications is assigned to a second machine, the computer program comprising computer program code which, when run on one of the machines causes the machine to:

receive a user command on the user interface of a first application based on the received user command, to generate a command message forward the generated command message via a command receiver to a container, in which the second set of applications are hosted execute the command on a receiving application in the container provide an integrated user interface for the first and second set of applications on the first machine.

Another example embodiment of the present invention refers to a computer program for executing the method for providing an integrated user interface of different applications, as mentioned above. Thus, another aspect of the invention is to be seen in a computer program being loadable in a memory of a computer, wherein the computer program is adapted to carry out the steps of the method as mentioned above.

The computer program may be stored on a computer readable memory or storage device.

Moreover, those skilled in the art will also appreciate that the functions explained herein below may be implemented using individual hardware circuitry, using software functioning in conjunction with a programmed microprocessor or general purpose computer, using an Application Specific Integrated Circuit (ASIC) and/or using one or more Digital Signal Processors (DSP). It will also be appreciated that the present invention may be embodied in a system comprising a computer processor and a memory coupled to the processor, wherein the memory is encoded with one or more programs that may perform the steps disclosed herein.

Generally, the method according to at least one embodiment of the invention may be executed on one single computer or on several computers that are linked over a network. The computers may be general purpose computing devices in the form a conventional computer, including a processing unit, a system memory, and a system bus that couples various system components including system memory to the processing unit. The system bus may be any one of several types of bus structures including a memory bus or a memory controller, a peripheral bus and a local bus using any of a variety of bus architectures, possibly such which will be used in clinical/medical system environments. The system memory includes read-only memory (ROM) and random access memories (RAM). A basic input/output system (BIOS), containing the basic routines that have the functionality to transfer information between elements within the computer, such as during start-up, may be stored in one memory.

Additionally, the computer may also include hard disc drives and other interfaces for user interaction. The drives and their associated computer-readable media provide non-volatile or volatile storage of computer executable instructions, data structures, program modules and related data items. A user interface may be a graphical user interface accompanied with a keyboard, a pointing device or other input devices (not shown in the figures), such as a microphone, a joystick, a mouse. Additionally, interfaces to other systems might be used, such as an interface to a radiological information system (RIS) or to a hospital information system (HIS) or PACS (Picture Archiving and Communication System). These and other input devices are often connected to the processing unit through a serial port interface coupled to system bus. Other interfaces include a universal serial bus (USB).

Moreover, a monitor or another display device is also connected to the computers of the system via an interface, such as video adapter. In addition to the monitor, the computers typically include other peripheral output or input devices (not shown), such as speakers and printers or interfaces for data exchange. Local and remote computer are coupled to each other by logical and physical connections, which may include a server, a router, a network interface, a peer device or other common network nodes. The connections might be local area network connections (LAN) and wide area network connections (WAN) which could be used within intranet or internet. Additionally networking environment typically includes a modem, a wireless link or any other means for establishing communications over the network.

Moreover, the network typically comprises at least one device for data retrieval, particularly for accessing data storage means like repositories and the like. Network data exchange may be coupled by the use of proxies and other servers.

FIG. 1 shows a setup with two machines M1, M2, each hosting different applications A. Preferably, two machines are used. However, it is also possible to have more than two machines hosting different sets of applications A. Each machine M1, M2 has a corresponding monitor, which is shown in FIG. 1 and which is associated to the respective machine via a communication interface (in FIG. 1 represented as cable). The left machine M1 represents the scanner control machine and the right machine M2 represents the machine for post processing or pre-processing, in particular of acquired scanner images. For the sake of clarity FIG. 1 only shows the monitors as a part of the user interface. It has to be noted that also other UI elements may be used, too, like a keyboard and a mouse or another pointing device, which are not shown in the figures.

This two machine setup is a typical deployment for the native.syngo based scanners where the scanner application (in FIG. 1 referred to as "App A") is running on the left monitor M1 and the syngo.via post-processing applications (in FIG. 1 referred to as "App B") are running on the right monitor M2. Although from architecture point of view both applications A are more or less independent and only loosely coupled through dedicated remote interfaces, according to the invention the user shall have the impression to work with one integrated application spanning over two monitors.

In the following some examples are given for illustration:

a. Access to the system is only allowed after a successful authentication. Therefore after start-up the scanner application presents a login dialog on the left monitor (associated to machine M1) while the syngo.via application shows a splash screen on the right monitor (associated to machine M2). Once a use has been authenticated by the scanner application, the splash screen gets removed from syngo.via and the same user identity is used in the scanner application and the post processing application.

b. If the user triggers a screen lock in the scanner application App A, the post processing application App B needs to be locked as well.

c. After a scan has been finished in the scan application App A, the correct/configured post processing application App B for that scan shall open automatically in syngo.via and the newly acquired images shall be displayed.

d. The scanner application App A allows the definition of auto routing rules for sending newly acquired images for example to the PACS (Picture Archiving and Communications Systems). Since DICOM functionality is only provided by syngo.via, the images are transferred to the syngo.via backend from where they are forwarded to the configured DICOM node.

The scenario described above with respect to the example of the "Job Viewer" application, which is an application of the second set of applications on the post-processing side (right machine M2), is described below in more detail with reference to FIG. 2.

In order to make that setup transparent, it is possible for a clinical user to monitor the status of the DICOM send Jobs from the scanner application App A by invoking the syngo.via Job Viewer (application) from the scanner application App A. The process of invoking the Job Viewer is shown in FIG. 2. The user controls the Job Viewer application only on the integrated user interface UI1, which is presented to the user on the monitor of the left machine M1.

Figure 2:
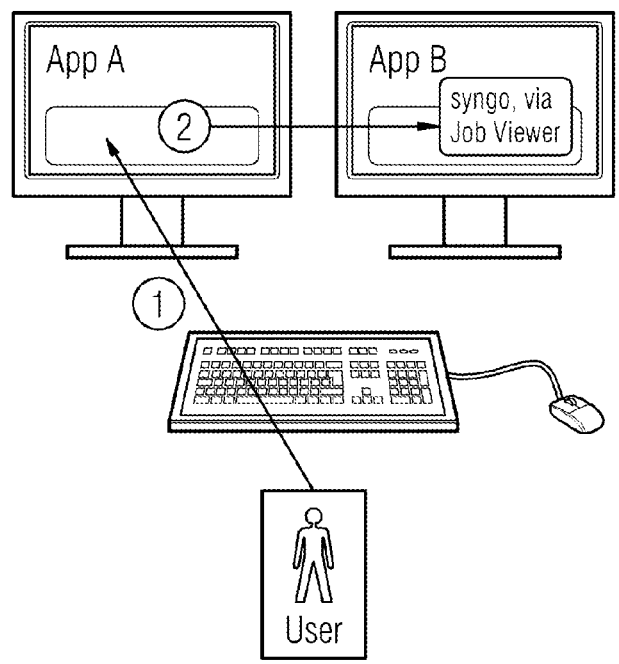
FIG. 2 is a schematic overview of an example application, wherein the user interface of the application has been integrated according to an embodiment the present invention.

In FIG. 2 there are depicted digit reference numerals in a circle. They are explained as follows:

| | |
|---|---|
| 1 | Get DICOM transfer status |
| 2 | Open Job Viewer and display DICOM Send Jobs for a dedicated patient. |

Figure 3:
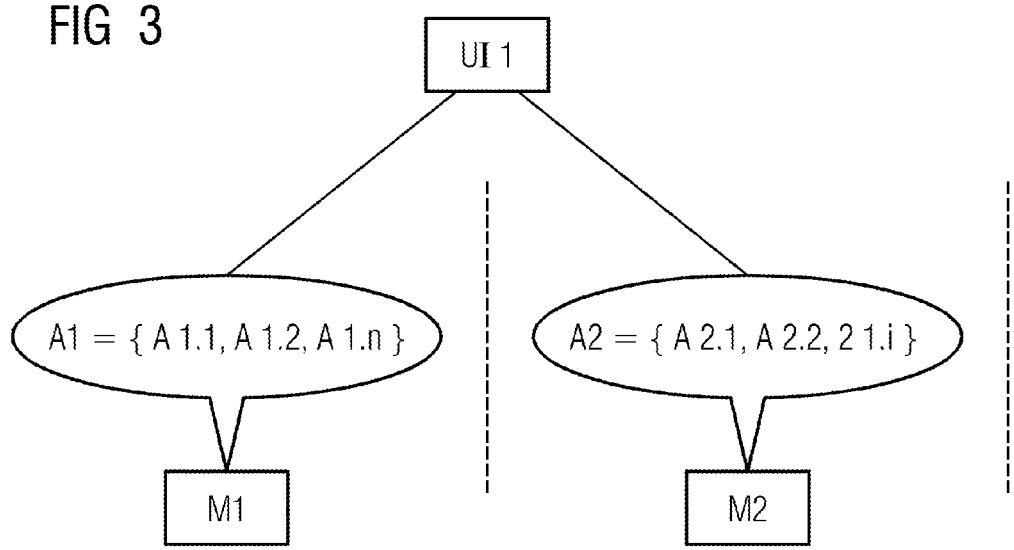
FIG. 3 is a schematic diagram showing the assignment of different sets of applications to different machines.

FIG. 3 shows a possible deployment in schematic form. The scanner machine M1 hosts a first set of applications A1, comprising different applications A 1.1, 1.2, 1.3 etc. The post-processing machine M2 (right side) hosts a second set of applications A2, comprising different applications A 2.1, 2.2, 2.3 etc. All the user interfaces for both sets of applications A1, A2 are integrated on one integrated user interface UI1, which is generated and provided on the left monitor of the scanner machine M1.

The system includes a Container EXE, which in the figures is represented by the reference numeral CONT and which provides a common runtime infrastructure for hosting applications. As part of provided runtime infrastructure, the Container CONT offers a set of services which can be accessed by applications running inside the Container CONT. Common examples for such services are logging of error/user messages, services for sharing context among the different applications etc.

Figure 4:
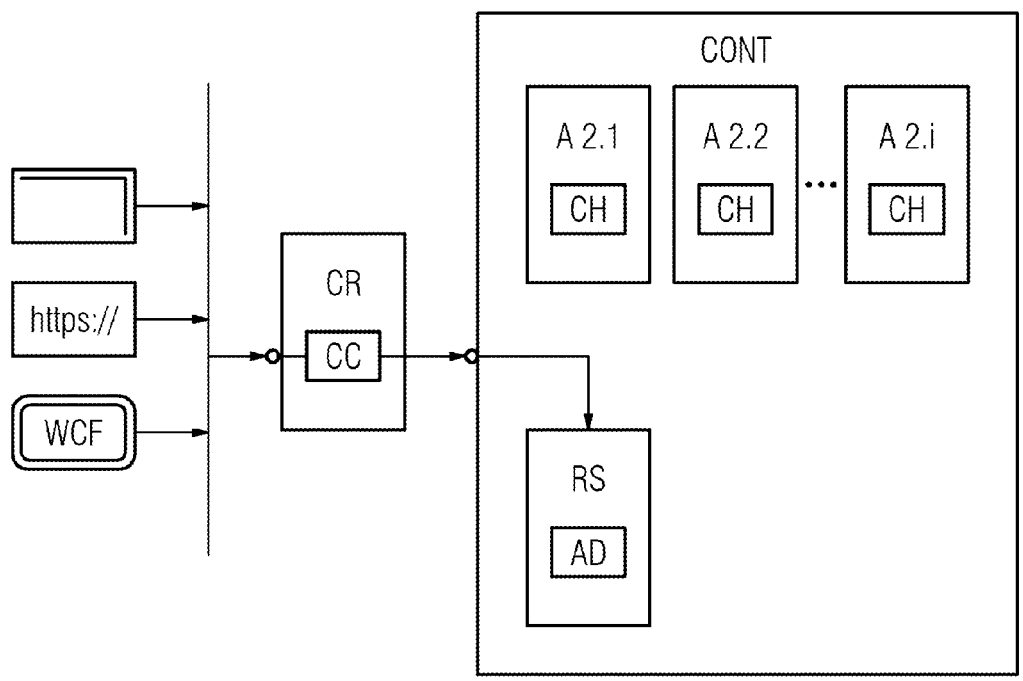
FIG. 4 is a schematic drawing of selected modules used for integrating user interfaces.

FIG. 4 shows other system components.

A Container Remoting Service RS, which provides two interfaces:
1) an internal interface through which applications/components running inside container CONT can register command handlers CH;
2) an external interface which allows applications running on the same machine M1/M2 to send commands to applications running inside the container CONT.

An Application Dispatcher AD within the Container Remoting Service RS is responsible for accepting the commands and for forwarding them to the Command Handler CH of the appropriate application.

A Command Receiver CR is a second process running on the same machine as the Container CONT. This component offers an interface which can be accessed by external applications through different protocols like http, local command line or WCF (Windows Communication Foundation), shown in FIG. 4 on the left side. External applications send messages that are targeted to application/components running inside the Container CONT to the Command Receiver CR. The Command Receiver CR is responsible to forward these messages to the Container CONT.

The process of registration of the Command Handlers CH is explained in more detail with respect to FIG. 5.

During the instantiation of an application in the Container CONT, the application can register a command handler CH at the Container Remoting Service RS. For that registration the application needs to provide
a) A name under which it should be accessible from the outside
b) A callback which will be invoked if a message is received for that application.

FIG. 5 shows the registration process by way of example for the Job Viewer application which has also been used previously. It is up to the application to define the actual functionality which it wants to offer for an external application. The Job Viewer might define commands for showing and hiding the Job Viewer user interface.

The lifecycle of the Command Receiver CR and the Container CONT are explained as follows.

Since the Command Receiver CR provides an interface to external applications its lifecycle should be bound to the lifecycle of the machine on which it provides the service—in other words the Command Receiver CR should be started automatically by the operating system (e.g. by configuring it as service/daemon or by utilizing the operating system's autostart functionality).

The Container CONT can be started either on demand by the user, automatically by the operating system or on demand by the Command Receiver CR, i.e. the Command Receiver CR checks whether a suitable Container CONT is running and triggers the start-up of the Container CONT if there is no such Container CONT running.

For systems where the on demand starting of the Container CONT is not required, the functionality of the Command Receiver CR could also be incorporated into the Container Remoting Service RS (which in turn means that the external interface provided by that Service would not be restricted to machine local communication any more).

FIG. 6 represents the invoking of a command from an external application.

To invoke a command provided by an application inside the Container CONT, the external application needs to construct a message which contains
The Name of the application to be triggered
The command to be executed by that application
Optional Parameters for the command.

Once the message has been constructed, the external application sends it to the Command Receiver CR. The Command Receiver CR checks whether the Container CONT is already running, and if not starts the Container CONT. Once the External Interface of the Container CONT is available, the Command Receiver CR forwards the request to the Container CONT. Inside the Container CONT the Application Dispatcher AD looks up the Command Handler CH of the affected Application and forwards the message to that Command Handler CH. The Command Handler CH parses the message and executes the requested functionality.

It is to be noted that this is a one-way communication without a back-channel for communicating back failure or success of the operations, i.e. the calling (external) application does not get back any response whether the message has been processed successfully or not.

FIG. 6 gives a more detailed view on the previously described process of invoking a command from an external application by doing a run-through with the Job Viewer example application. The Job Viewer application enables a user to see the DICOM send jobs for a dedicated patient. Also other examples of post-processing applications are within the scope of this application (e.g. reporting, lung care, liver care related applications, reconstructing images in different views etc.).

The circled numbers in FIG. 6 relate to the following operations.

| | |
|---|---|
| 3 | Get DICOM transfer status |
| 4 | Construct and send message via http |
| 5 | Forward message |
| 6 | Lookup Command Handler CH |
| 7 | Forward Action and Parameters. |

At least one embodiment of the present invention also provides a solution for context integration of multi applications A, which are distributed over different physical machines M1, M2.

The term "Application Context" relates to data or information, shared between distributed clustered applications A. An Application Context contains very general information like the ID of the logged in user as well as application specific information like the IDs of patients which require a specific handling within the application cluster (e.g. the scan patient). An Application Context is only accessible for an application within the cluster. Application outside of the cluster do not have access to it.

The following Application Context Manager Roles exist:
Local Application Context Manager LACM
The Local Application Context Manager LACM is responsible for sharing Application Context information between different components which are running within the same application process.
Machine Local Application Context Manager MLACM
The Machine Local Application Context Manager MLACM is responsible for sharing Application Context information between different processes running on the same physical machine.
Global Application Context Manager GACM
The Global Application Context Manager GACM is responsible for sharing Application Context information across one or more physical machines.

The following Context Types exist:
Local Application Context LAC, which is only shared between components within one process.
Machine Local Application Context MLAC, which is shared between processes running on one physical machine.
Global Application Context GAC, which is shared between applications running multiple physical machines which are connected via network.

Figure 7:
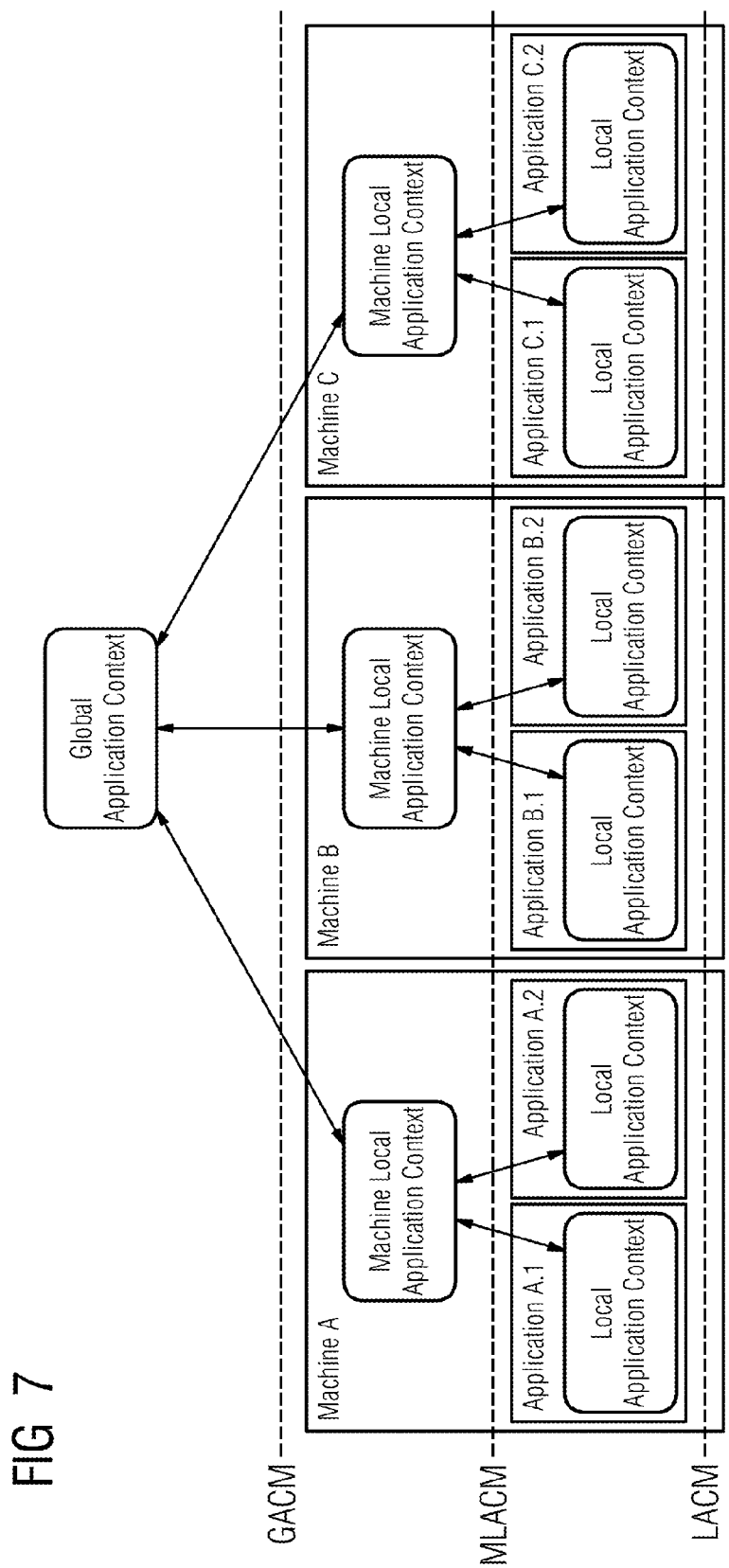
FIG. 7 depicts a logical hierarchy of the different types of contexts.

FIG. 7 depicts the logical hierarchy of the different types of contexts. It has to be noted that this image does not depict the actual hosting of the different application contexts.

Figure 8:
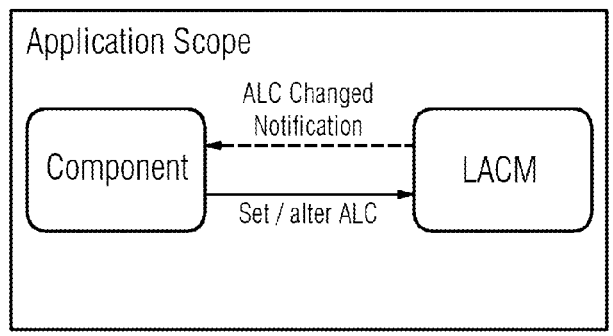
FIG. 8 depicts a scope of an application.

As can be seen in FIG. 8, components inside an application only directly interact with the Local Application Context Manager LACM. This means that a component calls an application programming interface API of the Local Application Context Manager LACM to set/alter context information. If context information changes, the Local Application Context Manager LACM sends an event to the component which contains information about what has actually changed within the Local Application Context LAC.

Not each and every context information is shared between all the different Context Managers but a Context Information Model defines on which level the data shall be shared:

Application Local Scope
Such information is only shared between components within the same application process, i.e. this information is only stored in the Local Application Context LAC.

Machine Local Scope
Such information is shared between applications running on the same physical machine, i.e. such information is stored in the Machine Local Application Context MLAC.

Global Scope
Such information is shared between one or more physical machines M1, M2.

The Information Model is either predefined for all Application Context Managers via configuration, i.e. each Application Context Manager "knows" which context data type belongs to which scope, or it can be defined during runtime by the component which stores data in the Local Application Context Manager LACM.

Figure 9:
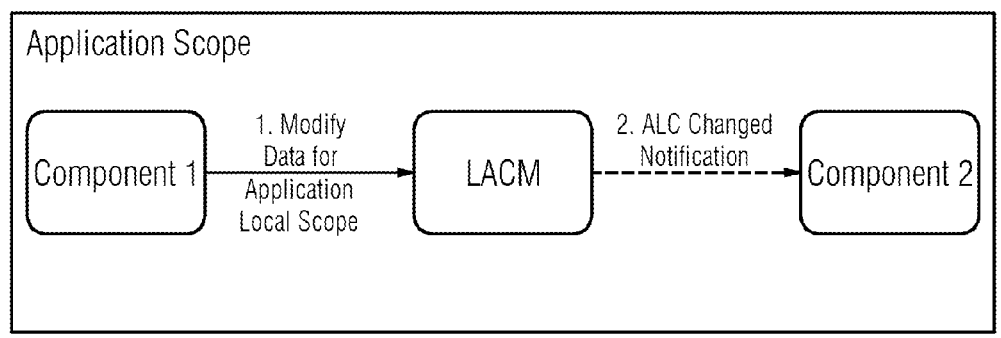
FIG. 9 depicts a process of changing context data.

FIG. 9 shows the process of changing context data which has been assigned to the Local Application Scope:
1. Component 1 modifies context data in the Local Application Context Manager LACM
2. Component 2 which is also registered at the Local Application Context Manager LACM receives a notification about the change. In FIG. 9 the continuous lined arrow refers to synchronous API calls and the dashed line refers to event notifications.

Figure 10:
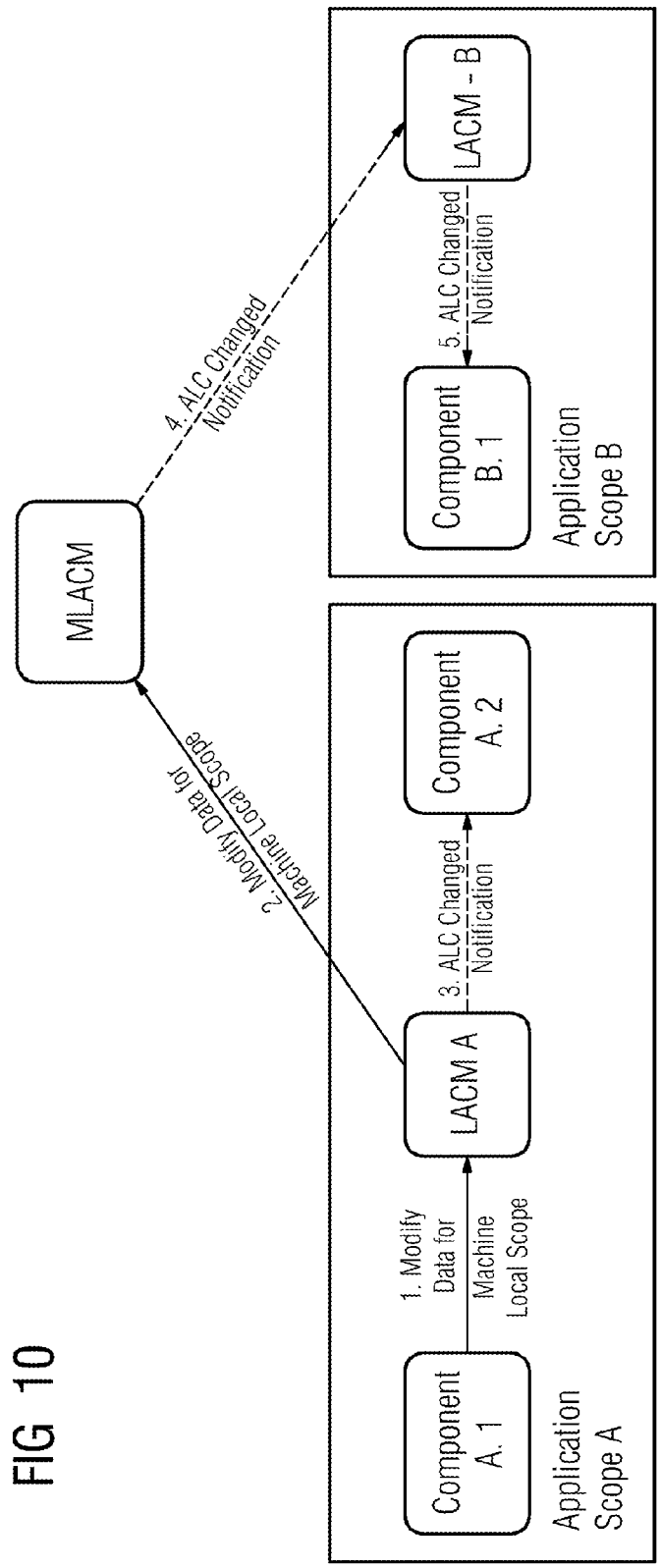
FIG. 10 depicts the process flow in case data with a Machine Local Scope is changed.

FIG. 10 depicts the process flow in case data with Machine Local Scope is changed:
1. Component A.1 of application A modifies context data which has been assigned to the Machine Local Scope
2. The Local Application Context Manager LACM, A updates the data in the Machine Local Application Context Manager MLACM.
3. The Local Application Context Manager LACM, A notifies all registered components about changed context data.
4. The Machine Local Application Context Manager MLACM informs the Local Application Context Managers LACM of other applications about the context data change.
5. The Local Application Context Managers LACM in the other application processes inform all registered components about the context data change. As in FIG. 9, also in FIG. 10 the continuous lined arrow refers to synchronous API calls and the dashed line refers to event notifications.

Figure 11:
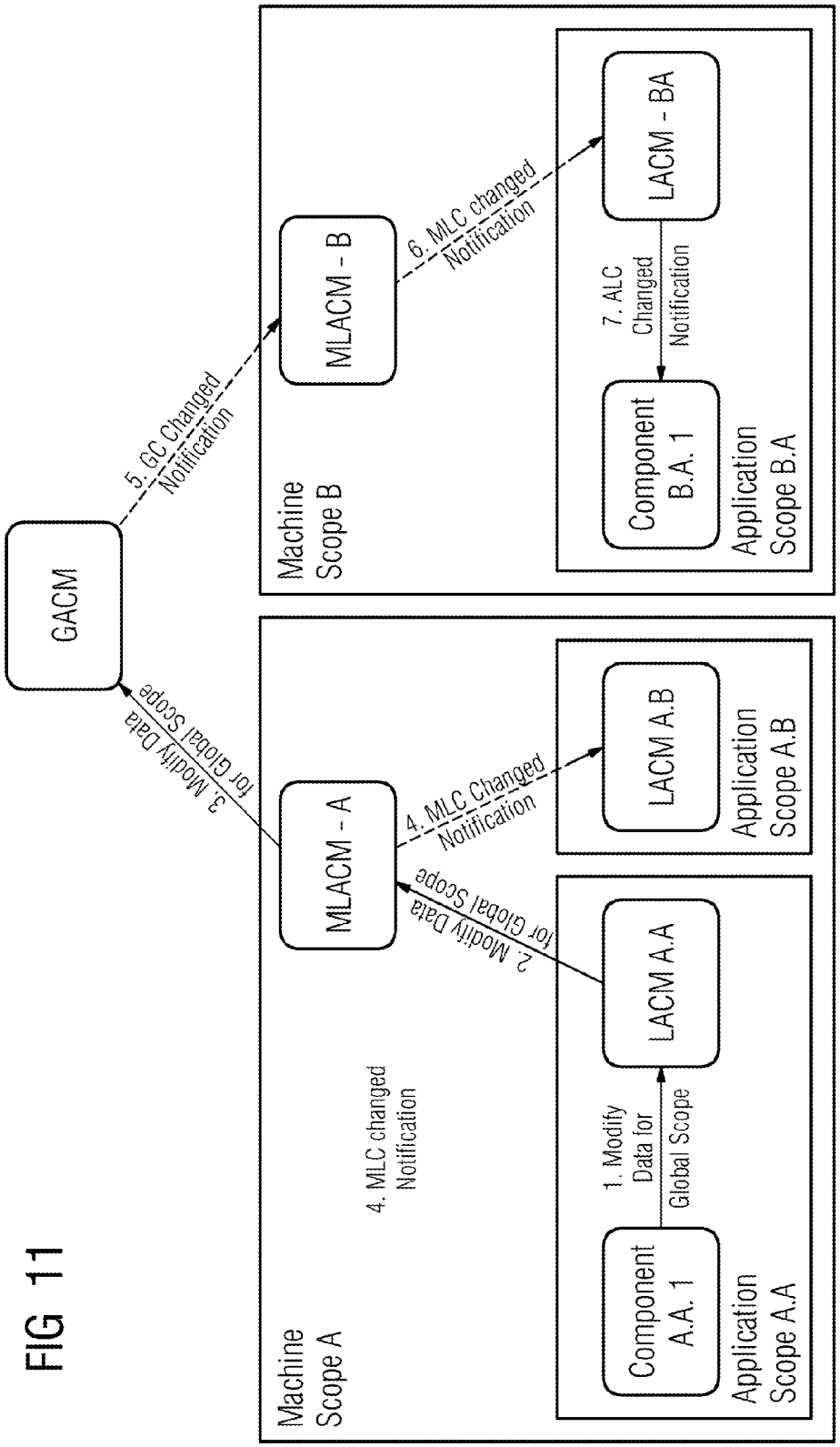
FIG. 11 depicts the process flow in case data with a Global Scope is changed.

FIG. 11 depicts how context data with Global Scope is changed:
1. Component A.A.1 modifies context data with Global Scope.
2. The Local Application Context Manager LACM A.A modifies the context data in the Machine Local Application Context Manager MLACM A. In addition the Local Application Context Manager LACM A.A informs all other components of Application A.A about the changed context information (not shown in the figure).
3. The Machine Local Application Context Manager MLACM A modifies the context data in the Global Application Context Manager GACM.
4. The Machine Local Application Context Manager MLCM A notifies all Local Application Context Managers LACM on Machine A about the changed data. The Machine Local Application Context Managers MLCM in turn inform all the registered components (not shown in the figure).
5. The Global Application Context Manager GACM informs all registered Machine Local Application Context Managers MLACM about the changed context data. It is to be noted that step 4 and 5 may occur in any arbitrary order.
6. The Machine Local Application Context Manager MLACM on each machine informs the registered Local Application Context Managers LACM about the changed context data.
7. Finally the Local Application Context Manager LACM within each application informs the registered components about the changed context data. In FIG. 11 the continuous lined arrow refers to synchronous API calls and the dashed line refers to event notifications.

Up to now only the logical structure/hierarchy of the Application Context Managers has been discussed. In fact the Application Context Manager Roles can be taken over by any application participating in the cluster.

Figure 12:
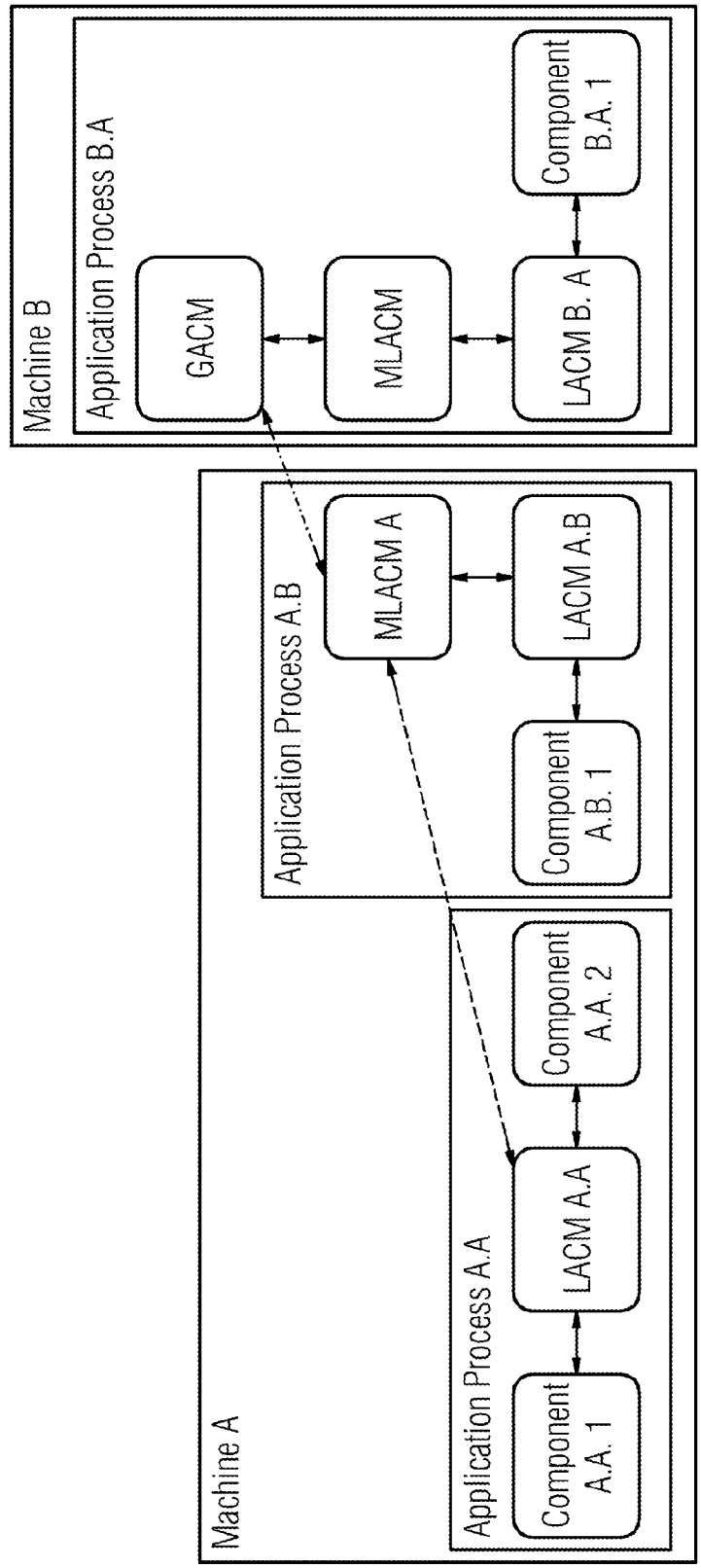
FIG. 12 depicts a possible deployment for the different machines.

In FIG. 12 two application processes are running on Machine A where Application A.B takes over the role of the Machine Local Application Context Manager MLACM for that machine. On machine B only one application process is running which takes over the responsibility for all three Application Context Manager Roles. In FIG. 12 the continuous lined double sided arrows refer to in process communication and the dashed line arrows refers to inter process communication and the dotted lined arrows refer to inter machine communication.

Figure 13:
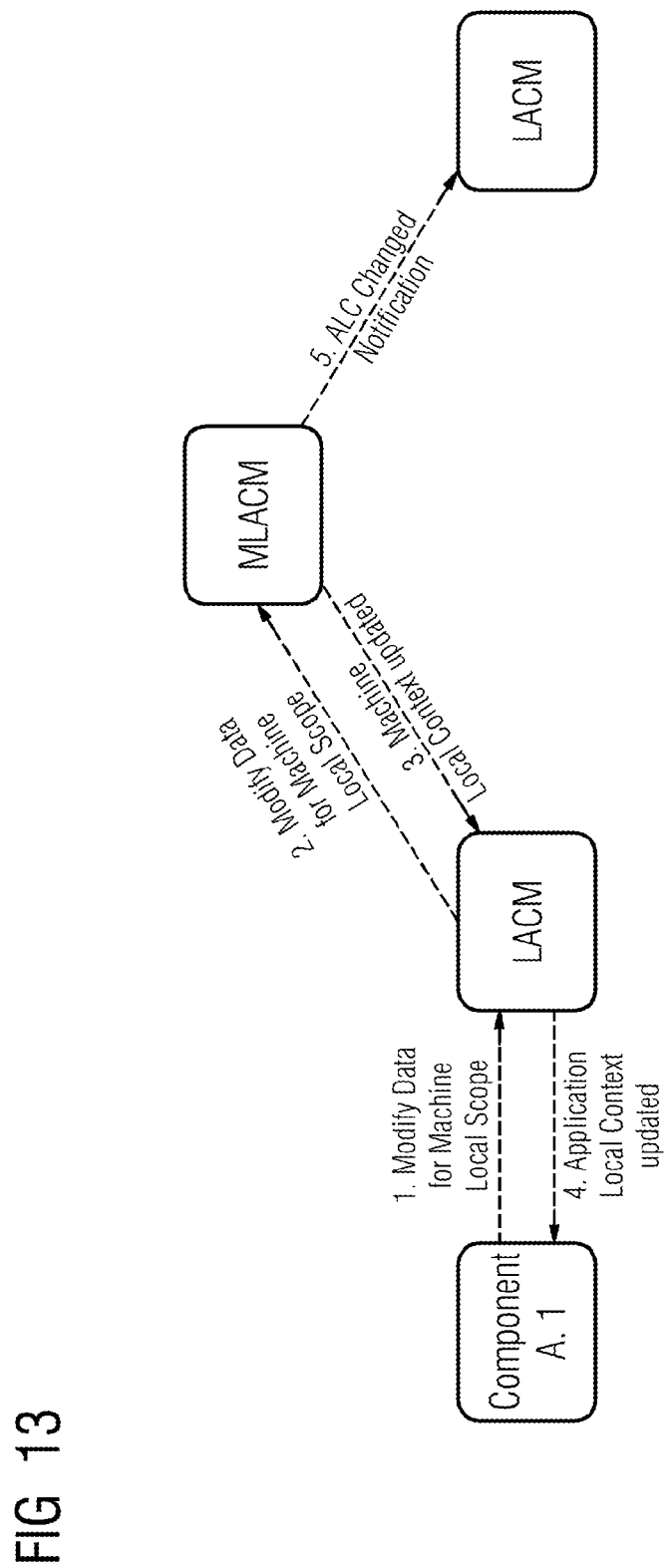
FIG. 13 depicts the implementation of a transactional approach with the process flow in case data with a Local Scope is changed.

FIG. 13 represents the transactional approach which is used for changing a context. However, the use of transactions is only an alternative mechanism. Transactions may be used in order to make sure that the a context change in fact is received or provided to the Machine Local Application Context Manager MLACM or to the Global Application Context Manager GACM.

As can be seen in the previous sections and in FIG. 13, changes in the Machine Local Application Context or in the Global Application Context may result in cross process/machine communication. This again means that race conditions may occur if two components in two different applications/machines try to manipulate the same application context data at the same time. Therefore it has to be distinguished between scenarios where only one component/application is driving changes for context data which is shared across several applications or machines several components of different applications drive changes of the same context data.

An example for the first scenario could be the user ID assuming that exactly one dedicated application is responsible for authenticating users and setting the user context. An example for the second scenario could be the Patient ID assuming different applications provide the possibility to select users from a user list and other applications should follow this selection.

For Application Context data belonging to the first category no special handling is required—since only one dedicated Component is responsible of setting and updating such data, not race conditions can occur.

Application Context data belonging to the second category can be supported with the help of transactions. The scope of the transactions corresponds to the scope of the Application Context data to be changed.

In FIG. 13 the dotted arrows on the left side of the Machine Local Context Manager MLACM depict the transaction:
1. A Component changes a context value which needs to be protected via a Transaction.
2. The Local Application Context Manager LACM modifies the context data in the Machine Local Application Context Manager MLACM.
3. The Machine Local Application Context Manager MLACM confirms the update.
4. The Local Application Context Manager LACM confirms the update
5. The Machine Local Application Context Manager informs other Local Application Context Managers LACM about the update. In FIG. 13 the continuous lined arrow refers to synchronous API calls and the dashed lined arrow refers to event notifications and the dotted arrows refer to transactions.

Other components trying to update the same Application Context data item while the transaction is still open will receive an error.

The process flow looks similar for Application Context data updates which are done on data items with Global Scope. The only difference in that case is that the transaction scope has to be extended up to the Global Application Context Manager.

Whether or not a data item has to be protected by a transaction can be specified via a flag in the Context Information Model, or it could be specified during runtime by the Components calling the APIs of the Local Application Context Manager LACM.

Persistency and Fault Recovery

The following error scenarios have to be considered:
1. Crash/unavailability of the Local Application Context Manager LACM.

Components registered at the Local Application Context Manager LACM should be notified if the Application Context Manager goes down. This is necessary to inform the user that no context changes can be triggered from the application any more. During start-up/restart the Local Application Context Manager LACM retrieves all context data with Machine Local Scope or Global Scope from the Machine Local Application Context Manager—so there is no need to persist this information as it can be retrieved during runtime. Context information with Application Local Scope can either be read from a persisted storage during the recovery phase or the application components resend this information once they register again at the Local Application Context Manager LACM.
2. Crash/unavailability of a Machine Local Application Context Manager.

If the Machine Local Application Context Manager MLACM crashes, all registered Local Context Application Managers LCAM have to be informed because a message has to be displayed to the user that cross process context sharing is not available on that machine. During restart of the Machine Local Application Context Manager MLACM it retrieves the Global Context information from the Global Application Context Manager GACM. Context information with Application Local Scope should either be read from a persisted storage or it is resend by Local Application Context Managers which reconnect to the Machine Local Application Context Manager. Inconsistencies could occur in the latter case if same Machine Local Application Context information has been changed in different Local Application Context Managers LACM while the Machine Local Application Context Manager MLACM was down. Strategies for resolving such inconstancies need to be considered.
3. Crash/unavailability of the Global Application Context Manger GACMM.

If the Global Application Context Manager GACM is down, all registered Machine Local Application Context Managers MLACM have to be informed. The Machine Local Application Context Managers MLACM in turn informs the registered Local Application Context Managers LACM so that all applications participating in the context sharing can inform the users about the unavailability of the Global Application Context. During restart the Global Application Context Manager GACM either reads the context information from a persisted storage or it retrieves the information again from the Machine Local Application Context Managers MLACM. In the latter case inconsistencies can occur which have to be resolved by appropriate strategies.

The following integration scenarios based on the Shared Context Manager according to this invention may be served.

1. Single Sign-On (shortly abbreviated with SSO) For achieving SSO between applications distributed across several machines, one application needs to take over the role of a master which performs the authentication and creates a shared User Context which contains information about the authenticated user.

Since all applications are shown on collocated monitors, the slave applications could show a splash screen as long as the Shared User Context has not been set to ensure that no access to the application is possible. This scenario is depicted in FIG. 14.

In FIG. 14 there are depicted digit reference numerals in a circle. They should refer to the sequence of steps and are explained as follows:

| 1 | Input LOGIN on the generated integrated user interface UI1 on the left monitor (related to the left machine M1) |
|---|---|
| 2 | Set User Context |

| | |
|---|---|
| 3 | Context Changed Notification |
| 4 | Hide Splash Screen. |

2. Single Sign-off/Screen Locking

FIG. 15 shows an example of a single sign-off or screen lock scenario in a schematic manner. The Single Sign-off from the applications or locking the screen is exactly the opposite of the Single Sign-On. The user triggers the action in the master which brings up the Login Dialog and deletes the User Context in the Global Application Context Manager GACM. As a result the slave application receives a Context Changed notification and displays the splash screen again. In FIG. 15 there are depicted digit reference numerals in a circle. They refer to the sequence of steps and are explained as follows:

| | |
|---|---|
| 1 | Input LOGOUT/LOCK SCREEN on the generated integrated user interface UI1 on the left monitor (related to the left machine M1) |
| 2 | Display Login Dialog |
| 3 | Delete User Context |
| 4 | Context Changed Information |
| 5 | Display Splash Screen. |

3. Aligned Visualization of Special Patients

Especially for scanner it's important to identify the current scan patient across master and slave. The way to achieve this is straight forward when using the Context Application Manager. Once a special treatment is selected for a patient, the Context Manager is updated. The receiving application (mostly the slave) reacts in an appropriate way (e.g. by highlighting the patient in the work list).

The example embodiments are to be considered in all respects only as illustrative and not restrictive. The scope of the invention is, therefore, indicated by the appended claims rather than by this description. All changes which come within the meaning and range of equivalency of the claims are to be embraced within their scope.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

REFERENCE NUMERALS

A medical application
A1 first set of applications, e.g. App A, with applications
  A1.1, A1.2, A1.3, . . . .

A2 second set of applications, e.g. App B, with applications A2.1, A2.2, A2.3, . . . .
M1 first machine
M2 second machine
CONT Container
RS Remoting Service
CH Command Handler
CR Command Receiver
CC Command Composer
Me Message
AD Application Dispatcher
A2.1 Job Viewer application
LorCH List of registered Command Handlers
UI1 Generated integrated user interface
GACM Global Application Context Manager
MLACM Machine Local Application Context Manager
LACM Local Application Context Manager or Application Local Application Context Manager
ALC Application Local Context

What is claimed is:

1. A system for integrating different user interfaces for different medical applications distributed across multiple physical machines, a first set of applications being assigned to a first machine and a second set of applications being assigned to a second machine, the system comprising:
one or more processors configured to execute computer-readable instructions to
provide a container, the container configured to provide a common runtime infrastructure for hosting applications, the applications including the first set of applications and the second set of applications,
enable the applications running inside the container to register a command handler for executing application logic,
provide a command receiver configured to receive commands input by a user interface of a first application among the first set of applications, and to interface to a second application among the second set of applications as a command is to be executed by the second application among the second set of applications,
share first context data across the multiple physical machines,
share second context data across different applications residing on a same physical machine, and
share third context data across different components running within a same application; and
an integrated user interface, for the first and second sets of applications, provided on the first machine; wherein
the container and the command receiver run on a same machine.

2. A system for integrating different user interfaces for different medical applications distributed across multiple physical machines, a first set of applications being assigned to a first machine and a second set of applications being assigned to a second machine, the system comprising:
one or more processors configured to execute computer-readable instructions to
provide a container, the container configured to provide a common runtime infrastructure for hosting applications, the applications including the first set of applications and the second set of applications,
enable the applications running inside the container to register a command handler for executing application logic,
provide a command receiver configured to receive commands input by a user interface of a first application among the first set of applications, and to interface to a second application among the second set of applications as a command is to be executed by the second application among the second set of applications,
share first context data across the multiple physical machines,
share second context data across different applications residing on a same physical machine, and
share third context data across different components running within a same application;
an integrated user interface, for the first and second sets of applications, provided on the first machine; and
wherein the command receiver is further configured to
receive the commands on the integrated user interface,
generate command messages in response to the received commands, and
forward the command messages to the applications running inside the container.

3. The system of claim 1, wherein the integrated user interface is shown on one common or on different monitors, related to the first machine.

4. The system of claim 1, wherein at least one of the first, second and third context data includes user context data and patient context data.

5. The system of claim 2, wherein
the container and the command receiver are run on a same machine.

6. The system of claim 1, wherein the container is started on demand by a user or automatically by an operating system.

7. The system of claim 1, wherein the first set of applications are medical scanner applications and the second set of applications are post-processing applications.

8. The system of claim 1, wherein the system is used for a single sign-on in which a user signs on to the second set of applications automatically by signing on to the first set of applications.

9. The system of claim 1, wherein the system is used for a single sign-off in which a user signs off from the second set of applications automatically by signing off from the first set of applications.

10. The system of claim 1, wherein the system is used for a single screen lock in which a user locks a screen in the second set of applications automatically by entering a screen lock command for the first set of applications.

11. The system of claim 1, wherein the one or more processors are further configured to execute computer-readable instructions to
automatically retrieve at least one of the first, second and third context data from a global context manager without re-authenticating the user in response to a system crash.

12. The system of claim 1, wherein the second set of applications includes a job viewer application and a show patient details application.

13. The system of claim 1, wherein
a respective lifecycle of at least one of the first, second and third context data is configured individually for each set of context data; and
non-volatile context data are provided persistently.

14. A computer-implemented method for integrating a user interface for a set of first applications and a set of second applications in a user interface for the set of first applications, the first and second applications being different medical applications distributed across multiple physical machines, the set of first applications being assigned to a first machine and the set of second applications being assigned to a second machine, the method comprising:

sharing context data across the multiple physical machines, across different applications residing on a same physical machine, and across different components running within a same application;

providing a container, the container being a common runtime infrastructure for hosting the set of first applications and the set of second applications;

enabling the set of first applications and the set of second applications running inside the container to register a command handler for executing application logic;

receiving, at a command receiver, a command on a user interface for a first application among the set of first applications, the command receiver interfacing with the container;

generating a command message based on the received command;

forwarding the generated command message to the container via the command receiver, wherein the container and the command receiver run on the second machine;

executing the received command on a second application among the set of second applications running inside the container; and integrating the user interface for the sets of first and second applications on the first machine.

15. A non-transitory computer-readable medium storing a computer program for integrating a user interface for a set of first applications and a set of second applications in a user interface for the set of first applications, the first and second applications being different medical applications distributed across multiple physical machines, the set of first applications being assigned to a first machine and the set of second applications being assigned to a second machine, the computer program comprising computer program code which, when run on a respective one of the first and second machines, causes the respective machine to perform a method comprising:

sharing context data across the multiple physical machines, across different applications residing on a same physical machine, and across different components running within a same application;

providing a container, the container being a common runtime infrastructure for hosting the set of first applications and the set of second applications;

enabling the set of first applications and the set of second applications running inside the container to register a command handler for executing application logic;

receiving, at a command receiver, a command on a user interface for a first application among the set of first applications, the command receiver interfacing with the container;

generating a command message based on the received command;

forwarding the generated command message to the container via the command receiver, wherein the container and the command receiver run on the second machine;

executing the received command on a second application among the set of second applications running inside the container; and integrating the user interface for the sets of first and second applications on the first machine.

16. The system of claim 8, wherein the system is used for a single sign-off in which a user signs off from the second set of applications automatically by signing off from the first set of applications.

17. The system of claim 8, wherein the system is used for a single screen lock in which a user locks a screen in the second set of applications automatically by entering a screen lock command for the first set of applications.

18. The system of claim 16, wherein the system is used for a single screen lock in which a user locks a screen in the second set of applications automatically by entering a screen lock command for the first set of applications.

19. The system of claim 5, wherein the container is started on demand by the command receiver.

\* \* \* \* \*